US011590027B2

(12) United States Patent
San et al.

(10) Patent No.: US 11,590,027 B2
(45) Date of Patent: Feb. 28, 2023

(54) METAL-DETECTABLE LENS ASSEMBLIES AND PROTECTIVE EYEWEAR INCLUDING SAME

(71) Applicant: Gateway Safety, Inc., Cleveland, OH (US)

(72) Inventors: Bonnie K. San, Berea, OH (US); Michael D. Love, Avon, OH (US)

(73) Assignee: Gateway Safety, Inc., Cleveland, OH (US)

( * ) Notice: Subject to any disclaimer, the term of this patent is extended or adjusted under 35 U.S.C. 154(b) by 0 days.

(21) Appl. No.: 17/014,524

(22) Filed: Sep. 8, 2020

(65) Prior Publication Data

US 2021/0069018 A1 Mar. 11, 2021

Related U.S. Application Data

(60) Provisional application No. 62/897,890, filed on Sep. 9, 2019.

(51) Int. Cl.
*A61F 9/02* (2006.01)

(52) U.S. Cl.
CPC ............... *A61F 9/029* (2013.01); *A61F 9/02* (2013.01)

(58) Field of Classification Search
CPC ........... A61F 9/02; A61F 9/029; G02C 5/001
USPC ..................................................... 2/426, 439
See application file for complete search history.

(56) References Cited

U.S. PATENT DOCUMENTS

| | | |
|---|---|---|
| 4,942,629 A | 7/1990 | Stadlmann |
| 5,018,223 A | 5/1991 | Gregory |
| 5,319,397 A | 6/1994 | Ryden |
| 6,010,220 A | 1/2000 | Smarto |
| 6,213,602 B1 | 4/2001 | Smarto |
| 6,769,767 B2 | 8/2004 | Swab et al. |
| 6,783,238 B1 | 8/2004 | Stepper |
| 6,824,265 B1 | 11/2004 | Harper |
| 7,004,581 B2 | 2/2006 | Landers |
| 7,104,645 B2 | 9/2006 | Pilat, Jr. |
| 7,241,007 B2 * | 7/2007 | Cody ....................... G02C 9/00 351/86 |
| D548,266 S | 8/2007 | Landers |
| 7,648,234 B2 | 1/2010 | Welchel et al. |
| 7,850,301 B2 | 12/2010 | DiChiara |
| 7,967,435 B1 * | 6/2011 | Seeto ...................... A61F 9/029 351/159.57 |
| 7,988,282 B2 | 8/2011 | Laustsen et al. |
| 8,342,679 B2 * | 1/2013 | Seeto ..................... G02C 5/008 351/41 |

(Continued)

FOREIGN PATENT DOCUMENTS

| | | |
|---|---|---|
| CN | 206757230 U | 12/2017 |
| CN | 209590443 U | 11/2019 |

(Continued)

*Primary Examiner* — F Griffin Hall
(74) *Attorney, Agent, or Firm* — Matthew P. Dugan

(57) ABSTRACT

Protective eyewear lens assemblies include one or more metal-detectable components and a lens body formed in-situ around the one or more metal-detectable components. The lens body is formed from a polymeric material such that the one or more metal-detectable component is permanently embedded within the lens body. Protective eyewear including such lens assemblies and methods of manufacture are also included.

20 Claims, 10 Drawing Sheets

(56) References Cited

U.S. PATENT DOCUMENTS

| | | | |
|---|---|---|---|
| 8,641,188 B2 * | 2/2014 | DiChiara | G02C 1/04 |
| | | | 351/86 |
| 9,229,248 B2 | 1/2016 | Kokonaski et al. | |
| 9,289,623 B2 | 3/2016 | Pugh et al. | |
| 9,366,882 B2 | 6/2016 | Iurilli | |
| 2007/0298242 A1 * | 12/2007 | Huo | G02C 7/108 |
| | | | 428/323 |
| 2013/0235328 A1 | 9/2013 | Cauvet et al. | |
| 2013/0271722 A1 | 10/2013 | DiChiara | |
| 2013/0342807 A1 | 12/2013 | Blum et al. | |
| 2016/0204839 A1 | 7/2016 | Liu et al. | |
| 2017/0068110 A1 | 3/2017 | Ho et al. | |
| 2021/0173232 A1 | 6/2021 | Wang et al. | |

FOREIGN PATENT DOCUMENTS

| | | |
|---|---|---|
| CN | 111273461 A | 6/2020 |
| FR | 1081963 A | 12/1954 |
| GB | 1183487 A | 3/1970 |

\* cited by examiner

METAL-DETECTABLE LENS ASSEMBLIES AND PROTECTIVE EYEWEAR INCLUDING SAME

This application claims the benefit of priority to U.S. Provisional Patent Application Ser. No. 62/897,890, filed on Sep. 9, 2019, the contents of which is hereby incorporated herein by reference in its entirety.

BACKGROUND

The subject matter of the present disclosure broadly relates to the art of personal protective equipment and, more particularly, to polymeric lens assemblies with one or more portions that include detectable quantities of metal as well as protective eyewear including one or more of such polymeric lens assemblies and methods of manufacturing polymeric lens assemblies and protective eyewear.

It is widely recognized and understood that manufacturing and agricultural facilities of a variety of types and kinds commonly utilize processing and/or conveying equipment during the manufacture of products. In some cases, one or more of these processing and/or conveying lines may be open to an open atmosphere, such as the interior of a building. As a non-limiting example, facilities that process meat or other foods often utilize long conveyor belts that have workers positioned along one or both sides of the conveyor belts performing various tasks in connection with the processing of the meat or other food products. In these and other cases, it may be possible for foreign objects and/or materials to inadvertently or otherwise enter the stream of food items being processed. To minimize the possibility of such foreign objects and/or materials from being incorporated into the final product, facilities commonly employ equipment and techniques to sense and thereby identify foreign material. As a non-limiting example, food items may be passed through one or more metal detectors to aid in identifying any foreign objects or materials at various stages throughout the process.

It has been recognized, however, that personal protective equipment is often manufactured from plastic materials, which are typically undetectable by conventional detection systems and/or processes. In some cases, one or more metal components have been added or otherwise assembled into personal protective equipment thereby rendering those products potentially detectable. To be suitable for use, however, lenses of protective eyewear are optically clear in at least one area so that the wearer can see through the lens of the protective eyewear. As such, known constructions of protective eyewear have relied upon metallic fasteners and/or rigid structural features made from metal to permit detection of the protective eyewear. However, in cases in which conventional protective eyewear is inadvertently broken and enters the stream of food items in one or more pieces, it may be possible for some of the pieces to pass undetected through any equipment or systems intended to identify such foreign objects or materials.

Accordingly, it is believed desirable to develop detectable lenses as well as protective eyewear including one or more of such lenses to aid in addressing the foregoing and/or other areas for improvement associated with detection of foreign objects and/or materials in connection with known manufacturing processes.

BRIEF SUMMARY

One example of a protective eyewear lens assembly in accordance with the subject matter of the present disclosure can include a metal-detectable component and a lens body formed in-situ around the metal-detectable component with the lens body formed from a polymeric material such that the metal-detectable component is permanently embedded within the lens body.

One example of protective eyewear in accordance with the subject matter of the present disclosure can include a lens assembly including a metal-detectable component and a lens body formed in-situ around the metal-detectable component. The lens body formed from a polymeric material such that the metal-detectable component is permanently embedded within the lens body. The lens body can extend in a widthwise direction between opposing first and second ends with a first hinge connection portion along the first end and a second hinge connection along the second end. The first and second hinge connections each unitarily formed from the polymeric material together with the lens body. A first temple can be pivotally attached to the first hinge connection of the lens body. A second temple can be pivotally attached to the second hinge connection of the lens body.

One example of a method of manufacturing a protective eyewear lens assembly in accordance with the subject matter of the present disclosure can include inserting a metal-detectable component into a mold cavity. The method can also include injecting a quantity of flowable polymeric material into the mold cavity and solidifying the flowable polymeric material into a lens body that includes at least one optically-transparent portion with at least a portion of the metal-detectable component permanently embedded within the polymeric material of the lens body. The method can further include removing the lens body and the metal-detectable component from the mold cavity as a protective eyewear lens assembly.

DETAILED DESCRIPTION

Figure 1:
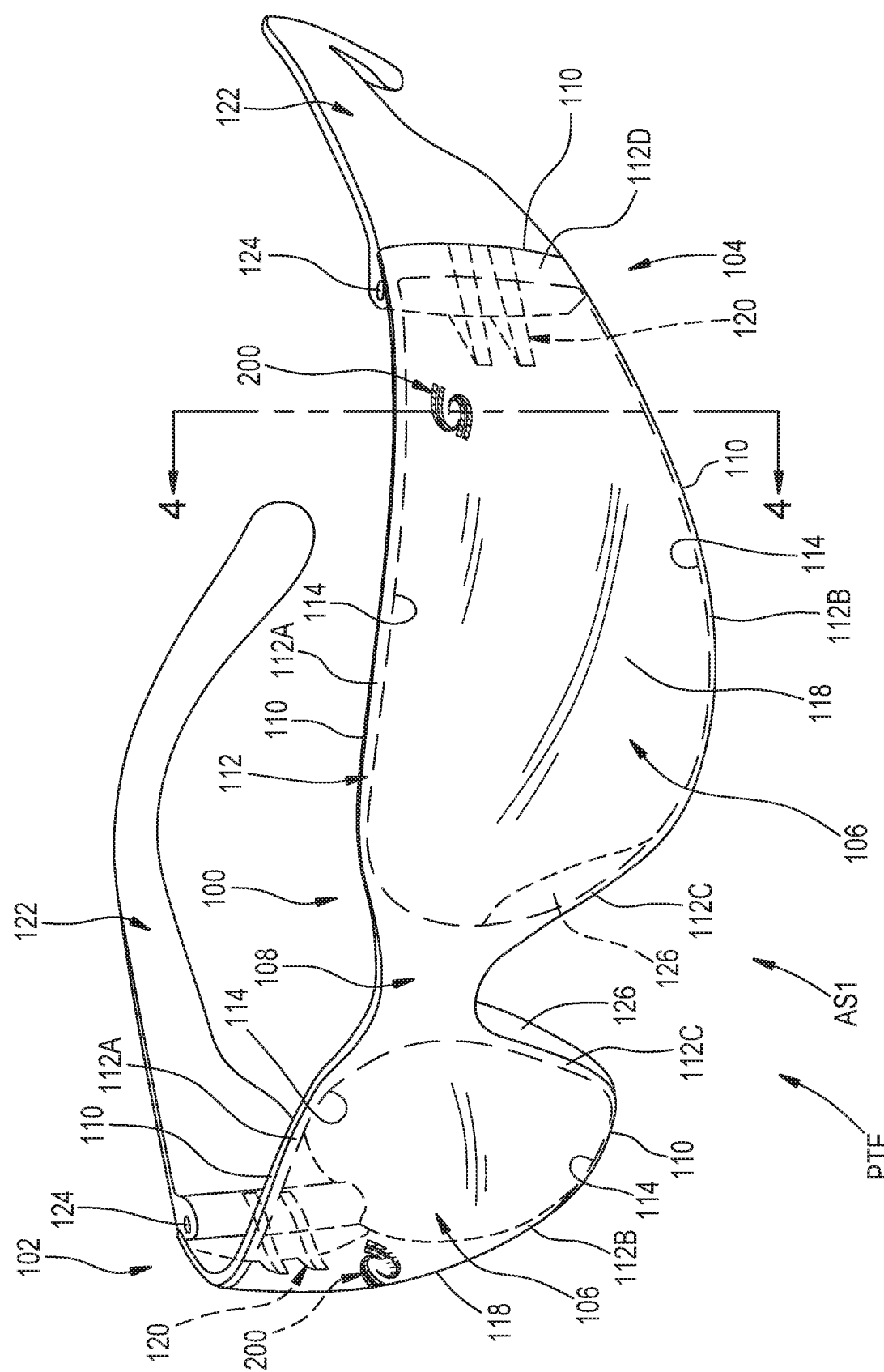
FIG. 1 is a top perspective view of one example of protective eyewear with a lens assembly in accordance with the subject matter of the present disclosure.

Turning now to the drawings, it is to be understood that the showings are for purposes of illustrating examples of the subject matter of the present disclosure and are not intended to be limiting. Additionally, it will be appreciated that the drawings are not to scale and that portions of certain features and/or elements may be exaggerated for purposes of clarity and/or ease of understanding.

In some cases, protective eyewear in accordance with the subject matter of the present disclosure can include two lens assemblies with one lens assembly supported on each side of the wearer's nose and in front of each of the wearer's eyes when the protective eyewear is being worn. In other cases, protective eyewear in accordance with the subject matter of the present disclosure can include a single lens assembly that is supported across the wearer's nose with a different portion of the lens assembly in front of each of the wearer's eyes when the protective eyewear is being worn. It is to be appreciated and distinctly understood that, while protective eyewear in accordance with the subject matter of the present disclosure are shown and described herein with reference to constructions including a single lens assembly, the subject matter of the present disclosure is equally applicable to protective eyewear including two lens assemblies and that the constructions and methods shown and described herein are merely exemplary and not intended to be limiting.

FIGS. 1-3 and 6-9 illustrate examples of protective eyewear PTE that includes at least one protective eyewear lens assembly in accordance with the subject matter of the present disclosure. The at least one lens assembly can include one or more lens components or bodies 100 that are at least partially formed from a polymeric material, such as an optically-transparent polycarbonate material, for example. Lens bodies 100 preferably include one or more optically-transparent portions that are positioned such that a wearer can look through the one or more optically-transparent portions in an otherwise typical fashion when the protective eyewear are in use. So, when in use in a conventional manner, protective eyewear PTE will be oriented such that lens body 100 has a top and a bottom spaced apart from one another in a heightwise direction with lens body ends 102 and 104 that are spaced apart from one another in a widthwise direction oriented transverse to the heightwise direction.

In the arrangements shown in FIGS. 1-15, lens body 100 includes optically-transparent portions 106 with a bridge portion 108 disposed therebetween. Lens body 100 also includes an outer peripheral edge 110. In some cases, optically-transparent portions 106 can at least partially define the outer peripheral edge. In other cases, lens body 100 can include a body periphery portion that at least partially defines the outer peripheral edge of the lens body. In some cases, the body periphery portion can form a substantially contiguous border or band around lens body 100. In other cases, the body periphery portion can include two or more separate or discrete segments. In either case and as non-limiting examples, lens body 100 can include a body periphery portion 112 that can include one or more segments 112A of body periphery portion 112 disposed along top or upper portions of the outer peripheral edge. Body periphery portion 112 can also include one or more segments 112B disposed along bottom or lower portions of the outer peripheral edge. Body periphery portion 112 can further include one or more segments 112C disposed along inward portions of the outer peripheral edge, such as may be adjacent bridge portion 108, for example. Body periphery portion 112 can also include one or more segments 112D disposed outward of segments 112C in the widthwise direction, such as along ends 102 and 104, for example.

Optically-transparent portions 106 can be disposed inward of outer peripheral edge 110 and/or body periphery portion 112. In some cases, body periphery portion 112 and/or any one or more of segments 112A-D thereof can include or otherwise be at least partially formed from a material that is separate and distinct from the material of optically-transparent portions 106 and/or bridge portion 108. In other cases, body periphery portion 112 can be unitarily formed with optically-transparent portions 106 and/or bridge portion 108 from a common polymeric material. In such cases, body periphery portion 112 can, optionally, be frosted, colored, opaque or otherwise less optically-transparent than portions 106 and/or 108. As such, it will be appreciated that in any construction in accordance with the subject matter of the present disclosure a visible demarcation line may, in some cases, be present where optically-transparent portions 106 transition into body periphery portion 112 (and/or any one or more of segments 112A-D thereof), such as is represented in FIGS. 1-9 by intersection or dashed line 114, for example.

It will be appreciated that lens bodies 100 can include one or more inside surface portions 116 facing toward the user when protective eyewear PTE is being worn and one or more outside surface portions 118 facing away from the user when the protective eyewear is being worn. Ends 102 and 104 are disposed adjacent or otherwise along optically-transparent portion 106 in a direction outboard of or otherwise spaced outward of bridge portion 108. It will be appreciated that the lens body ends are spaced apart from one another in the widthwise direction with bridge portion 108 disposed therebetween such that one of optically-transparent portions 106 is disposed between the bridge portion and one of lens body ends 102 and/or 104. Additionally, lens bodies 100 can include a pivot or hinge connection 120 disposed on or along body ends 102 and/or 104, such as on or along segments 112D of body periphery portion 112, for example. In a preferred arrangement, hinge connections 120 are unitarily formed from a common polymeric material with optically-transparent portions 106, bridge portion 108 and/or body periphery portion 112.

Protective eyewear PTE can also include any suitable number of one or more additional features and/or components. As a non-limiting example, protective eyewear PTE can include temples 122 secured in a suitable manner on or along opposing ends 102 and 104 of lens body 100. As one non-limiting example, temples 122 can be pivotally connected or otherwise secured to hinge connections 120 of lens body 100 using a suitable fastener 124, such as a pin, screw, rivet, or other connection, for example. In some cases, such a pin, screw, rivet, or other fastener may be formed from a metal material. As another example, protective eyewear PTE can, in some cases, include one or more nose pads 126 disposed below bridge portion 104 to support protective eyewear PTE on the nose of a wearer in an otherwise conventional fashion. In some cases, nose pads 126 can be provided separately from lens body 100 and can be secured thereto in a suitable manner. In other cases, the nose pads can be unitarily formed from a common polymeric material with optically-transparent portions 106, bridge portion 108 and/or body periphery portion 112.

In accordance with the subject matter of the present disclosure, a lens assembly of protective eyewear PTE also includes one or more metal-detectable components (which are also referred to herein as "metal-detectable inserts") disposed along the lens body (or bodies). In a preferred arrangement, one or more of the detectable components are at least partially embedded, encased and/or otherwise captured on, along and/or within the lens body (or bodies). Additionally, in a preferred arrangement, one or more of the detectable components can be of a size, shape and/or configuration that provides negligible strength, stiffening and/or other structural support to the lens body (or bodies). Furthermore, the one or more metal-detectable components are preferably permanently attached (i.e., inseparable without damage, destruction or material alteration of at least one of the component parts) to the lens body (or bodies).

Figure 4:
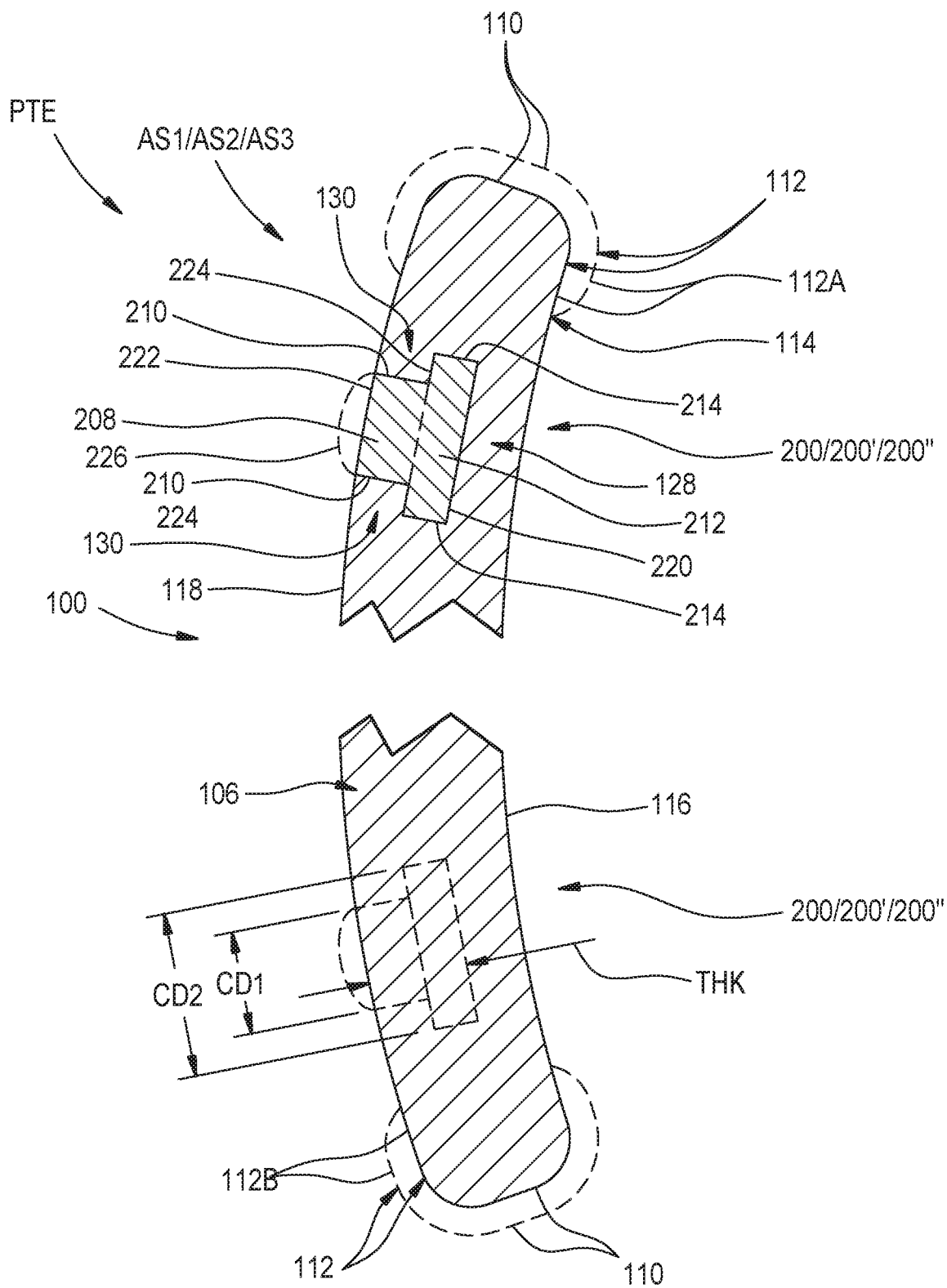
FIG. 4 is a cross-sectional side view of the exemplary lens assemblies shown in FIGS. 1-3 taken from along lines 4-4 therein.
Figure 5:
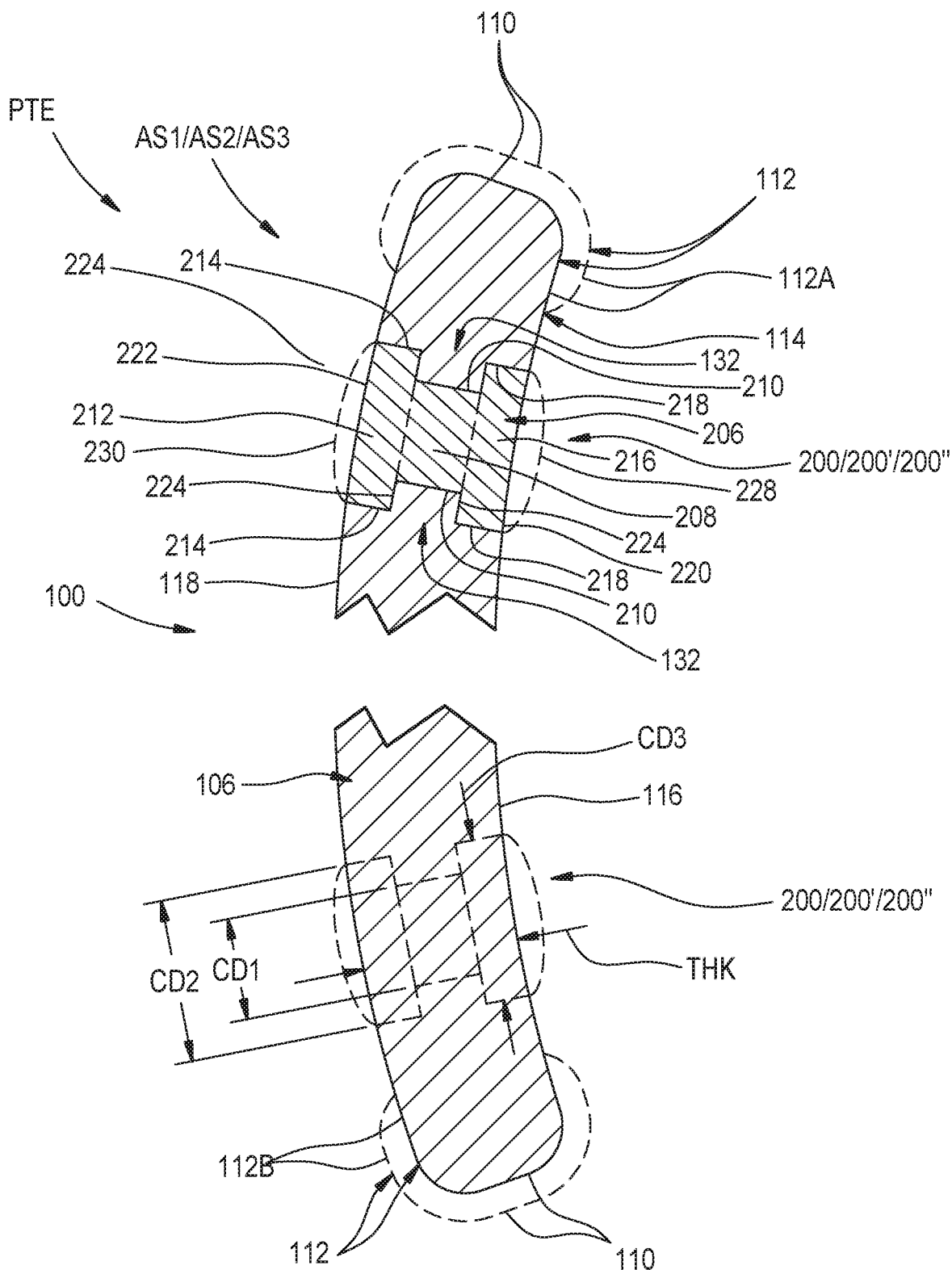
FIG. 5 is a cross-sectional side view of an alternate construction of the lens assemblies in FIGS. 1-4.

As one non-limiting example, a protective eyewear lens assembly AS1 in accordance with the subject matter of the present disclosure is shown in FIGS. 1, 4 and 5 as including lens body 100, as shown and described above, and one or more metal-detectable components 200 that are at least partially embedded, encased and/or otherwise captured on, along and/or within lens body 100. That is, metal-detectable component 200 is, preferably, at least partially embedded, encased and/or otherwise captured on, along and/or within the constituent material of lens body such that a surface (or surface portion) of each of the detectable components is exposed along the inside surface, the outside surface or both the inside and outside surfaces of lens body 100. It will be appreciated that detectable components 200 can be of any suitable size, shape and/or configuration, such as may include any one or more of logos, symbols, geometric elements and/or characters. In a preferred arrangement, at least one of metal-detectable components 200 is included on or along each side (in the widthwise direction) of lens body 100 such that upon being separated into two pieces, such due to a disconnection along bridge portion 108, for example, each of the two pieces will include at least one of metal-detectable component 200.

Figure 2:
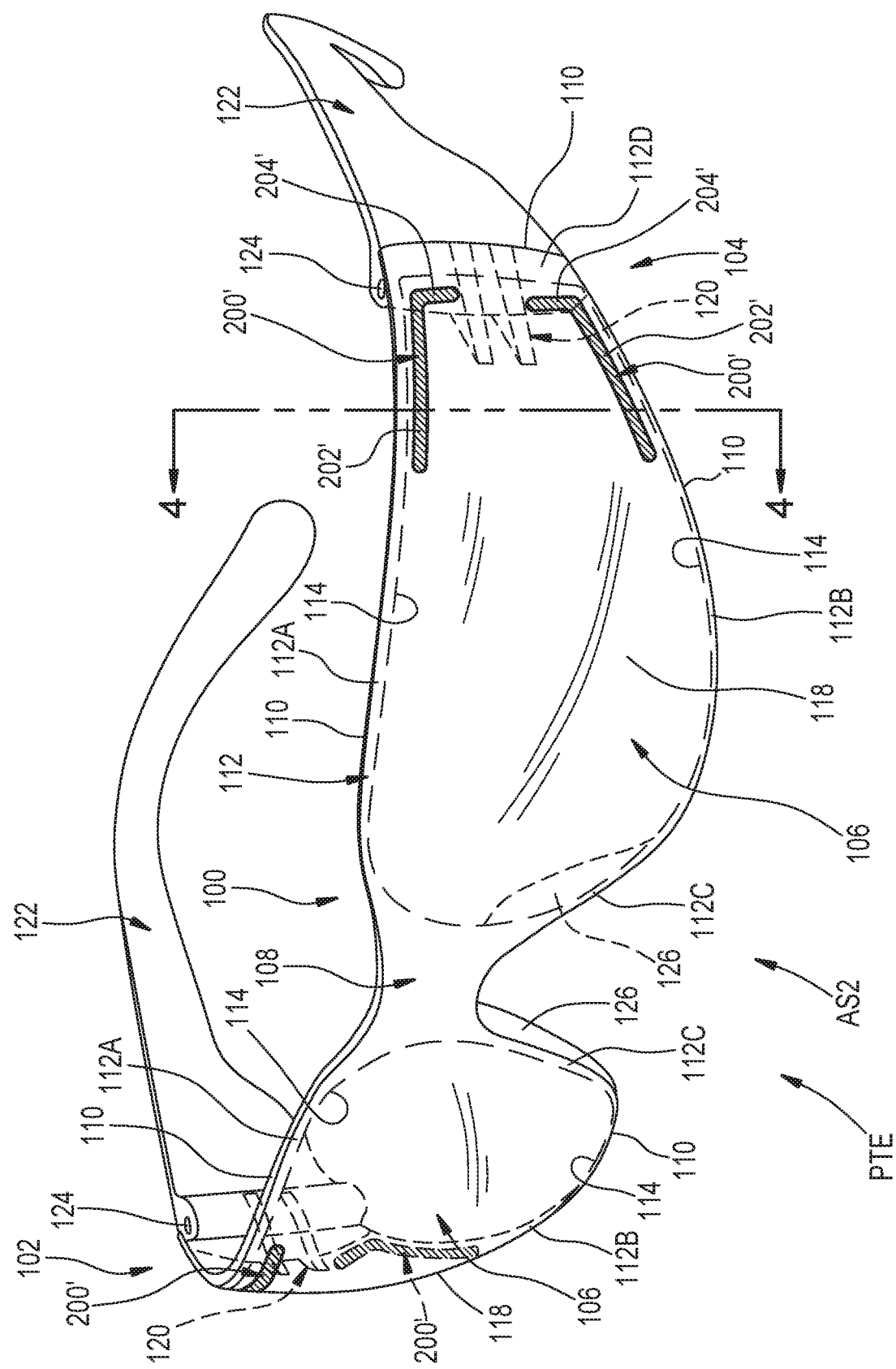
FIG. 2 is a top perspective view of another example of protective eyewear with a lens assembly in accordance with the subject matter of the present disclosure.

As another non-limiting example, a protective eyewear lens assembly AS2 in accordance with the subject matter of the present disclosure is shown in FIGS. 2, 4 and 5 as including lens body 100, as shown and described above, and one or more metal-detectable components 200' that are at least partially embedded, encased and/or otherwise captured on, along and/or within lens body 100. Metal-detectable components 200' are at least partially embedded, encased and/or otherwise captured on, along and/or within the lens body such that a surface (or surface portion) of each of the detectable components is exposed along the inside surface, the outside surface or both the inside and outside surfaces of lens body 100. Metal-detectable components 200' differ from metal-detectable components 200, shown and described in connection with FIG. 1, in that metal-detectable components 200' include an elongated length of metal-detectable material (e.g., a metal material and/or a metal-infused polymeric material) with at least a first elongated portion 202' and a second elongated portion 204' oriented transverse to first elongated portion 202'. In a preferred arrangement, first elongated portion 202' can extend adjacent and/or otherwise along a first part of body periphery portion 112 (e.g., one of segments 112A and/or 112B). Additionally, or in the alternative, second elongated portion 204' can extend adjacent and/or otherwise along a part of body periphery portion 112 (e.g., one of segments 112C and/or 112D). In a preferred arrangement, at least one of metal-detectable components 200' is included on or along each side (in the widthwise direction) of lens body 100 such that upon being separated into two pieces, such due to a disconnection along bridge portion 108, for example, each of the two pieces will include at least one of metal-detectable component 200'. In the exemplary arrangement shown in FIG. 2, lens assembly AS2 includes four metal-detectable components 200' with two of the metal detectable components disposed along each side of bridge portion 108 in the widthwise direction toward outward each of segments 112D. Additionally, two of metal detectable components 200' are disposed along the upper portions of outer peripheral edge 110 (e.g., along segments 112A) and two of metal detectable components 200' are disposed along the lower portions of outer peripheral edge 110 (e.g., along segments 112B). It will be appreciated, however, that other configurations and/or arrangements can be used without departing from the subject matter of the present disclosure.

Figure 3:
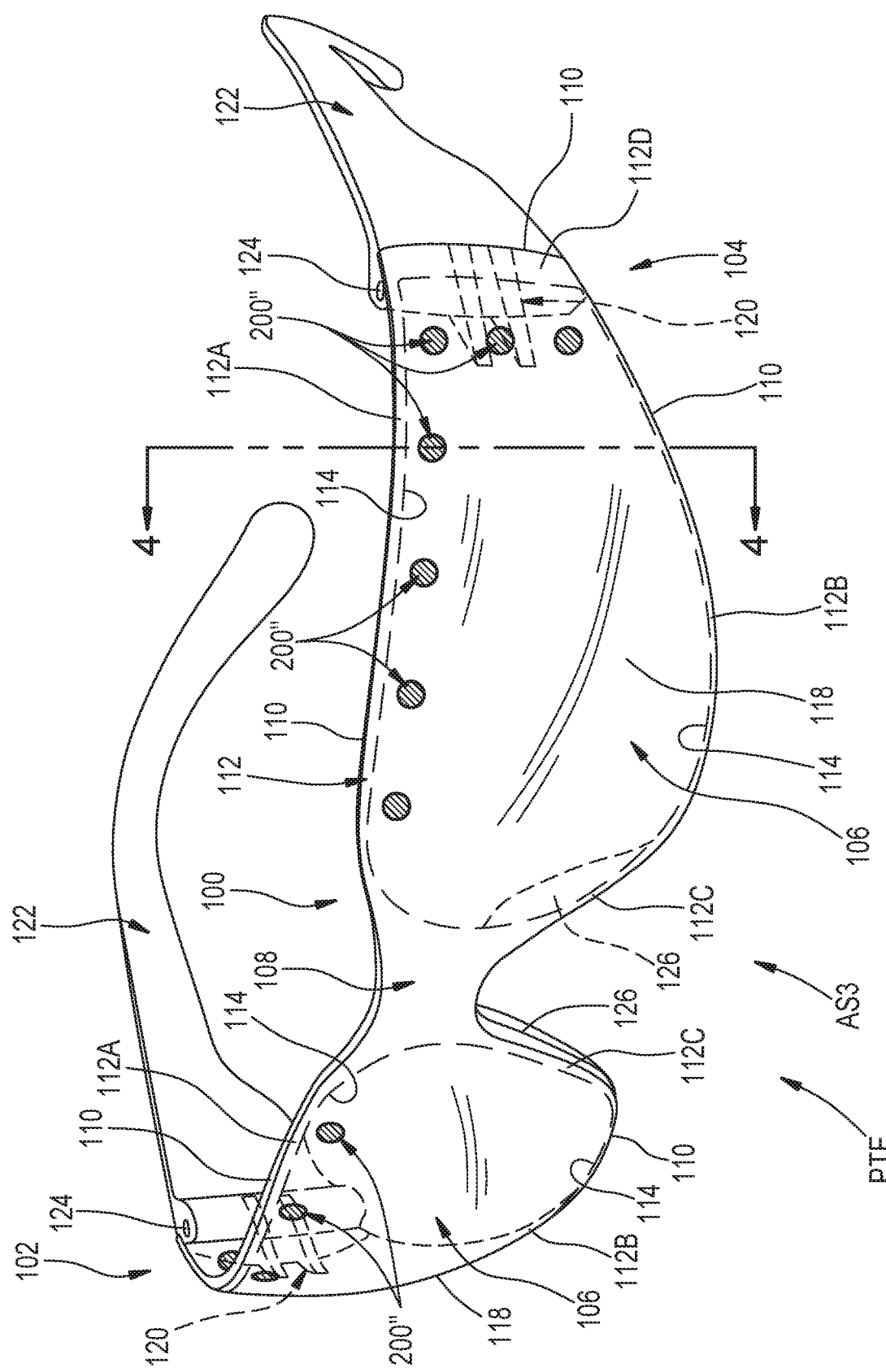
FIG. 3 is a top perspective view of a further example of protective eyewear with a lens assembly in accordance with the subject matter of the present disclosure.

As a further non-limiting example, a protective eyewear lens assembly AS3 in accordance with the subject matter of the present disclosure is shown in FIGS. 3-5 as including lens body 100, as shown and described above, and one or more metal-detectable components 200" that are at least partially embedded, encased and/or otherwise captured on, along and/or within lens body 100. Metal-detectable components 200" are at least partially embedded, encased and/or otherwise captured on, along and/or within the lens body such that a surface (or surface portion) of each of the detectable components is exposed along the inside surface, the outside surface or both the inside and outside surfaces of lens body 100. Metal-detectable components 200" differ from metal-detectable components 200, shown and described in connection with FIG. 1, and from metal-detectable components 200', shown and described in connection with FIG. 2, in that metal-detectable components 200" include a plurality of metal-detectable material (e.g., a metal material and/or a metal-infused polymeric material) that are spaced apart from one another along a common part of body periphery portion 112 (e.g., along at least one of segments 112A, 112B, 112C and/or 112D). As one non-limiting example, lens assembly AS3 can include three (3) or more metal-detectable components 200 disposed in spaced relation to one another one or along a common part of body periphery portion 112. In a preferred arrangement, a plurality of metal-detectable components 200" are included on or along each side (in the widthwise direction) of lens body 100 such that upon being separated into two pieces, such due to a disconnection along bridge portion 108, for example, each of the two pieces will include two or more metal-detectable components 200". In the exemplary arrangement shown in FIG. 5, lens assembly AS3 includes fourteen (14) metal-detectable components 200" with seven (7) of the metal detectable components disposed along each side of bridge portion 108 in the widthwise direction and with two or more of the metal detectable components positioned along segments 112A and 112D. It will be appreciated, however, that other configurations and/or arrangements can be used without departing from the subject matter of the present disclosure.

With reference, now, to FIGS. 4 and 5, metal-detectable components 200, 200' and/or 200" can include a component body 206 that is at least partially formed from a magnetically-detectable and/or otherwise metal-detectable material (e.g., a metal material and/or a metal-infused polymeric material). In addition to the arrangement and/or configuration of metal-detectable components 200, 200' and/or 200", component bodies 206 thereof are configured to be at least partially embedded, encased and/or otherwise captured on, along and/or within lens body 100 such that the lens body and one or more metal-detectable components are permanently attached (i.e., inseparable without damage, destruction or material alteration of at least one of the component parts) to one another. Component bodies 206 have a cross-sectional shape with a thickness extending through lens body 100 in a direction transverse to the heightwise and widthwise directions, as is represented in FIGS. 4 and 5 by reference dimension THK. Component bodies 206 also include a body portion 208 with a cross-sectional dimension CD1 between side surface portions 210 that face away from one another. Component bodies 206 can also include a body portion 212 with a cross-sectional dimension CD2 between side surface portions 214 that face away from one another with cross-sectional dimension CD2 being greater than cross-sectional dimension CD1 (e.g., an approximately T-shaped configuration). As shown in FIG. 5, component bodies 206 can, in some cases, include a body portion 216 that is disposed along body portion 208 opposite body portion 212 (e.g., an approximately H-shaped configuration). Body portion 216 extends between side surface portions 218 that face away from one another with a cross-sectional dimension CD3 that is greater than cross-sectional dimension CD1. In some cases, cross-sectional dimensions CD2 and CD3 can have an approximately common size or value.

Component bodies 206 also include an inside surface portion 220 oriented toward inside surface portion 116 of lens body 100. Component bodies 206 can further include an outside surface portion 222 oriented toward outside surface portion 118 of the lens body. Additionally, component bodies 206 can include one or more intermediate surface portions 224 disposed between inside surface portion 220 and outside surface portion 222 (i.e., in the thickness direction). It will be appreciated that intermediate surface portions 224 in FIG. 4 are due, at least in part, to the difference between cross-sectional dimensions CD1 and CD2 with intermediate surface portions 224 in FIG. 4 facing away from inside surface portion 116 of lens body 100. Intermediate surface portions 224 in FIG. 5 are due, at least in part, to the difference between cross-sectional dimension CD1 and cross-sectional dimensions CD2 and CD3 with intermediate surface portions 224 in FIG. 5 facing toward one another such that a space or channel (not numbered) is formed therebetween that is disposed inwardly of inside and outside surface portions 220 and 222 in the thickness direction. Furthermore, it will be appreciated that the intermediate surface portions shown in FIG. 5 are approximately the same size and shape due, at least in part, to the common differences between cross-sectional dimension CD1 and cross-sectional dimensions CD2 and CD3. In some cases, however, intermediate surface portions of different sizes and/or shapes can be used. Further still, in some two or more separate intermediate surface portions can extend at least partially along the component body (e.g., one above and one below body portion 208 in FIG. 4). In other cases, an intermediate surface portion can cover a substantially-contiguous area that extends along and/or around body portion 208.

As discussed above, metal-detectable components are at least partially embedded, encased and/or otherwise captured on, along and/or within the lens body (or bodies) such that the metal-detectable components are permanently attached (i.e., inseparable without damage, destruction or material alteration of at least one of the component parts) to the lens body. In the arrangement shown in FIG. 4, outside surface portion 222 of component body 206 is exposed on or along outside surface portion 118 of lens body 100. In some cases, outside surface portion 222 can have a shape and/or contour that approximately matches that of outside surface portion 118 of lens body 100. In other cases, outside surface portion 222 of component body 206 can be approximately planar, recessed into and/or projecting outwardly beyond outside surface portions 118, such as is collectively represented in FIG. 4 by dashed lines 226. Additionally, inside surface portion 220 of component body 206 in FIG. 4 is disposed between the inside and outside surface portions of lens body 100. In such an arrangement, a portion 128 of lens body 100 is disposed between inside surface portion 116 and inside surface portion 220 and a portion 130 of lens body is disposed between intermediate surface portion 224 and outside surface portion 118 such that metal-detectable inserts 200, 200' and 200" are captured within lens body 100 between the inside and outside surface portions thereof.

In the arrangement shown in FIG. 5, inside surface portion 220 of component body 206 and outside surface portion 222 of the component body are respectively exposed on or along inside and outside surface portions 116 and 118 of lens body 100. In some cases, surface portions 220 and/or 222 can have a shape and/or contour that approximately matches that of inside surface portion 116 and/or outside surface portion 118, respectively. In other cases, the inside surface portion and/or the outside surface portion of component body 206 can be approximately planar, recessed into and/or projecting outwardly beyond outside surface portions 118, such as are collectively represented in FIG. 5 by dashed lines 228 and 230, respectively. It will be appreciated that in such an arrangement, the space or channel formed between intermediate surface portions 224 in FIG. 5 will be disposed between inside and outside surface portions 116 and 118. A portion 132 of lens body 100 is disposed within the channel between the intermediate surface portion thereby capturing metal-detectable components 200, 200' and 200" within lens body 100 between the inside and outside surface portions thereof. For example, in some cases, the metal-detectable components can have an approximately circular shape (e.g., in FIG. 3) with the space or channel in component bodies 206 taking the form of an annular groove. It will be appreciated, however, that other configurations and/or arrangements can alternately be used.

Figure 6:
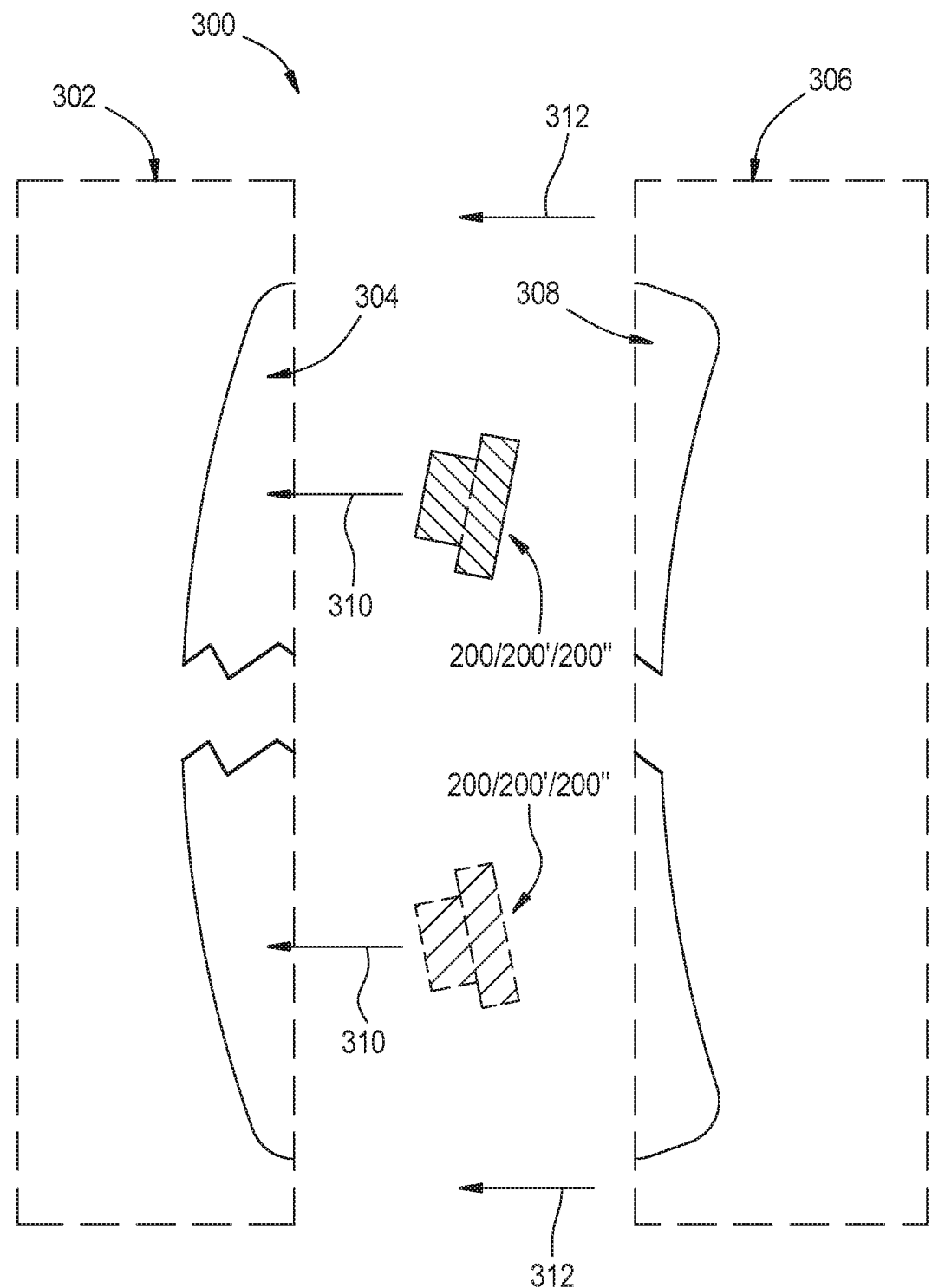
FIG. 6 is a schematic representation of a mold assembly shown in an open condition and prior to insertion of a metal-detectable component during manufacture of an exemplary lens assembly in accordance with the subject matter of the present disclosure, such as are shown in FIGS. 1-5, for example.
Figure 7:
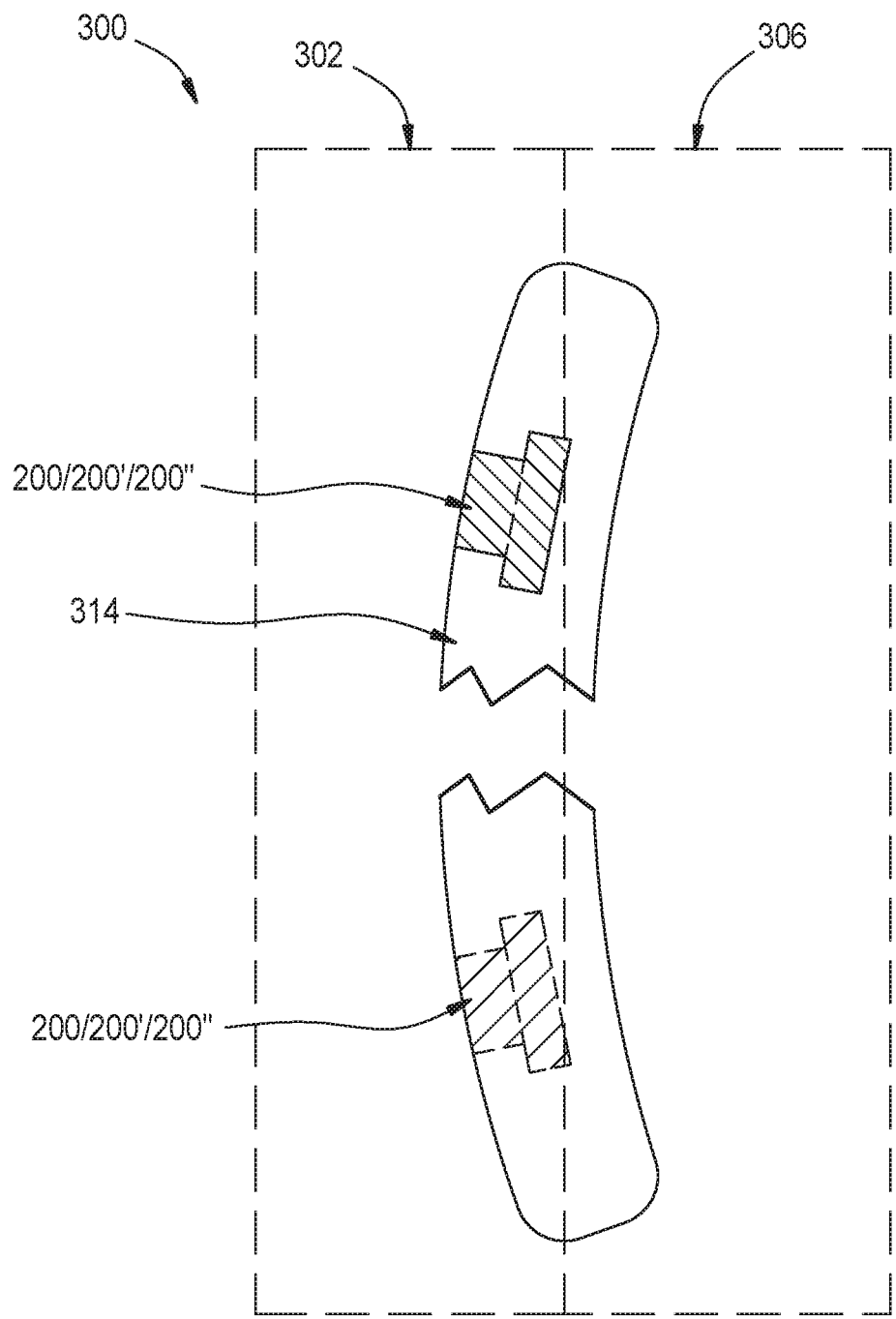
FIG. 7 is a schematic representation of the exemplary mold assembly in FIG. 6 shown in a closed condition with a metal-detectable component captured within the mold cavity prior to manufacture of an exemplary lens assembly, such as is shown in FIGS. 1-5, for example.
Figure 8:
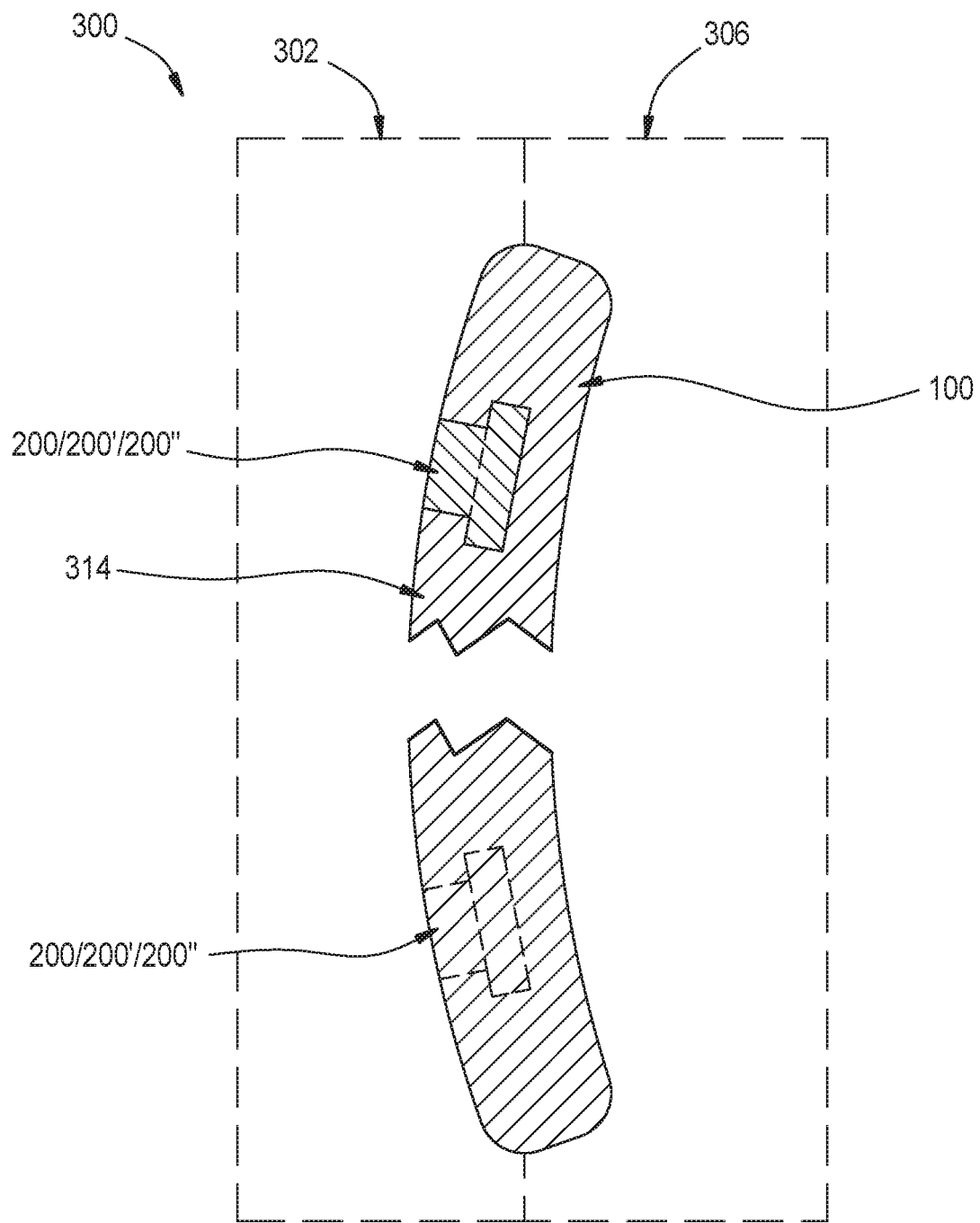
FIG. 8 is a schematic representation of the mold assembly in FIG. 7 with a lens body of the exemplary lens assembly formed in situ to encase at least the metal-detectable component.
Figure 9:
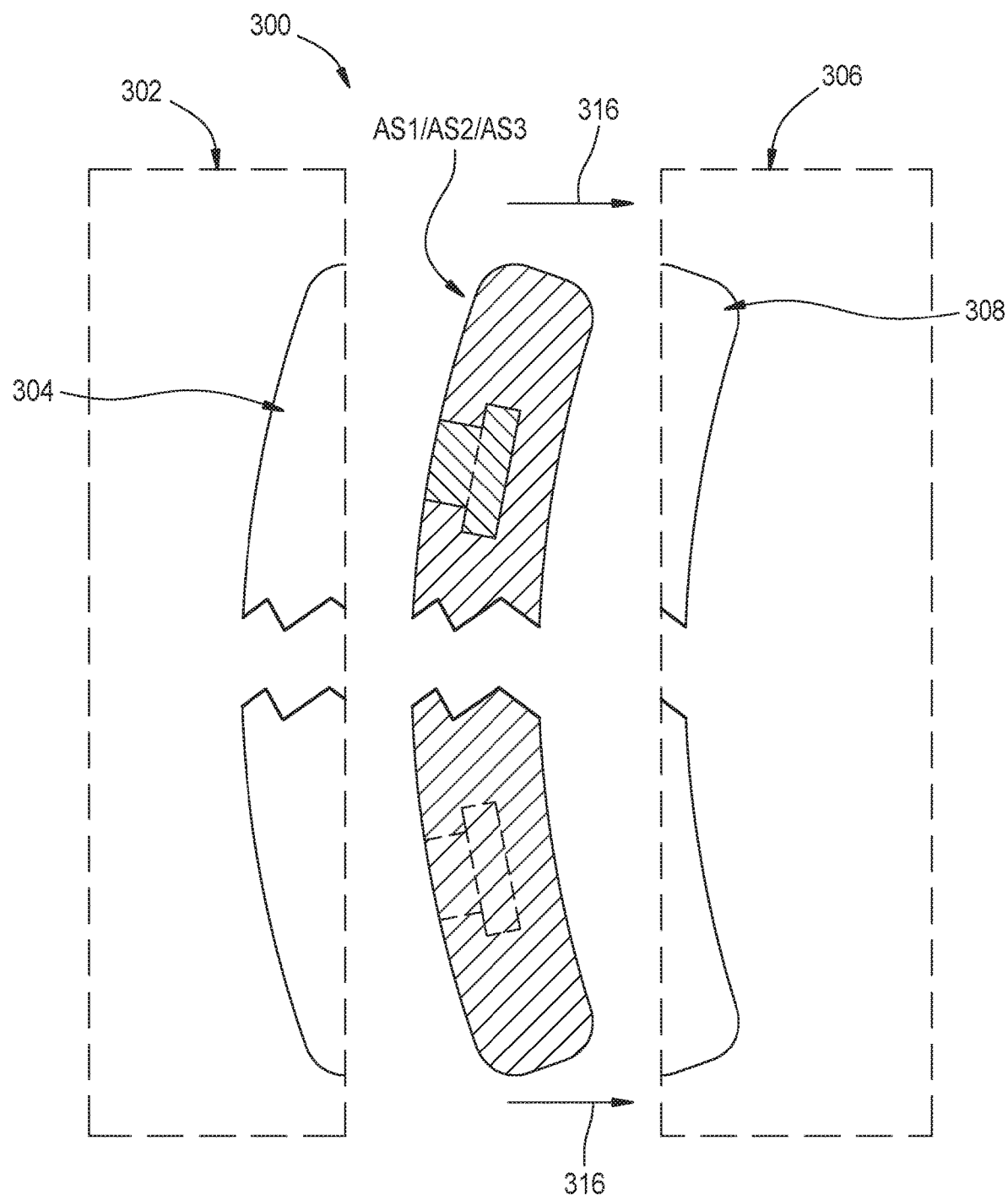
FIG. 9 is a schematic representation of the mold assembly in FIG. 8 with the completed lens assembly ejected from the mold cavity.

FIGS. 6-9 schematically illustrate a method of manufacturing a protective eyewear lens assembly (e.g., lens assemblies AS1, AS2 and AS3) in accordance with the subject matter of the present disclosure. One non-limiting example of a mold assembly 300 is schematically shown that includes a mold section 302 with a mold cavity portion 304 and a mold section 306 with a mold cavity portion 308. Mold sections 302 and 306 are shown spaced apart from one another in FIG. 6 such that any combination of one or more of metal-detectable components 200, 200' and/or 200" can be inserted into mold cavity portion 304 and/or 306, as is represented in FIG. 6 by arrows 310. Mold assembly 300 can then be closed by moving mold sections 302 and 306 toward and into engagement with one another, as is represented by arrows 312, such that mold cavity portions 304 and 308 are joined together to form a mold cavity 314. With reference to FIG. 7, in a closed condition of mold assembly 300, metal-detectable components 200, 200' and/or 200" are captured and/or otherwise retained in a predetermined and substantially fixed position within mold cavity 314. A quantity of flowable polymeric material can then be injected or otherwise flowed into mold cavity 314 around the combination of one or more of metal-detectable components 200, 200' and/or 200". The flowable polymeric material is then cooled or otherwise allowed to solidify into lens body 100 that together with the combination of one or more of metal-detectable components 200, 200' and/or 200". In this manner, lens body 100 is formed in-situ with at least a portion of one or more of metal-detectable components 200, 200' and/or 200", which are permanently embedded within the polymeric material of the lens body, to at least partially form one of lens assemblies AS1, AS2 and/or AS3. The lens assembly is then ejected or otherwise removed from mold assembly 300 by separating mold sections 302 and 306, as is represented by arrows 316 in FIG. 9.

Figure 10:
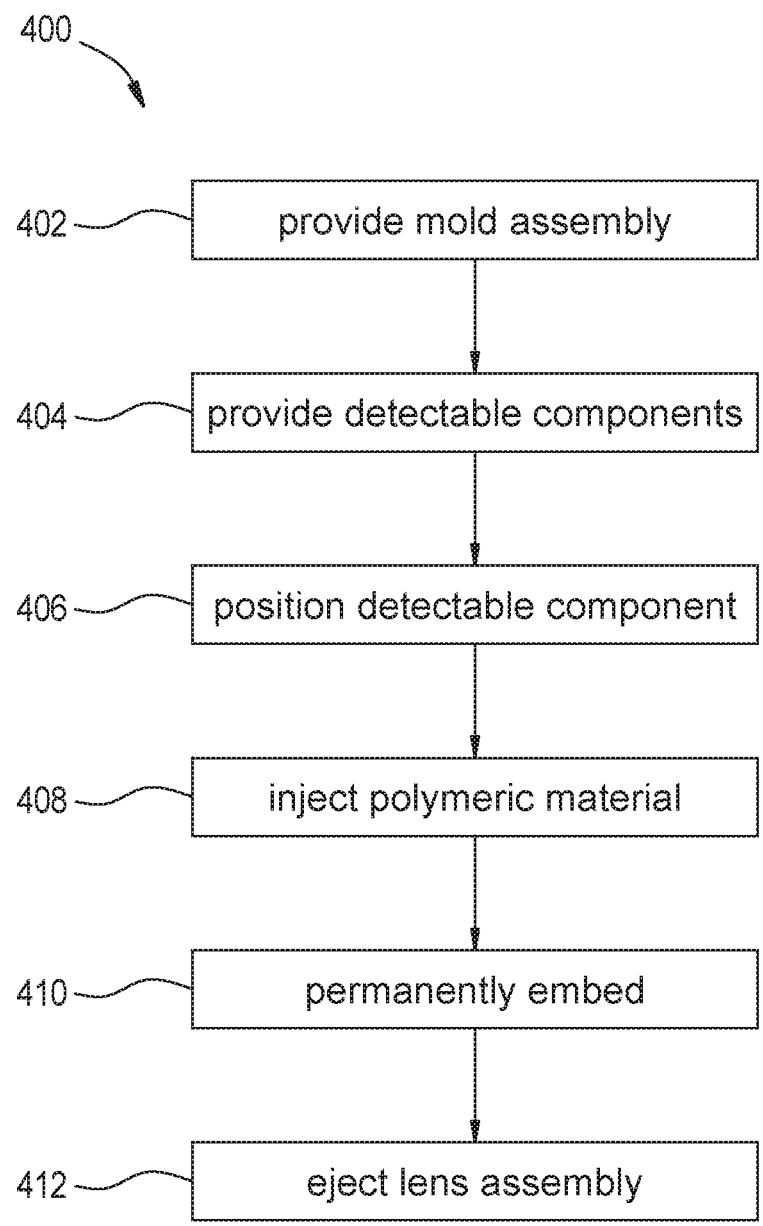
FIG. 10 is a graphical representation of one example of a method of manufacturing metal-detectable protective eyewear in accordance with the subject matter of the present disclosure.

FIG. 10 graphically illustrates one example of a method 400 in accordance with the subject matter of the present disclosure of manufacturing protective eyewear, such as protective eyewear PIE, for example. As shown therein, method 400 can include providing a mold assembly that includes a mold cavity, such as mold assembly 300 with mold cavity 314, for example, as is represented in FIG. 10 by box 402. Method 400 can also include providing one or more metal-detectable components, such as any combination of one or more of metal-detectable components 200, 200' and/or 200", for example, and inserting the one or more metal-detectable components in a predetermined and substantially-fixed position within the mold cavity, as are represented in FIG. 10 by boxes 404 and 406, respectively. Method 400 can further include injecting a quantity of flowable polymeric material into the mold cavity and around the one or more metal-detectable components, as is represented in FIG. 10 by box 408. Method 400 can also include cooling or otherwise solidifying the polymeric material into the lens body in-situ with the one or more of metal-detectable components, which are then permanently embedded within the polymeric material of the lens body, as is represented by box 410. The lens body together with the one or more metal-detectable components can then be ejected or otherwise removed from the mold assembly as lens assemblies (e.g., lens assemblies AS1, AS2 and/or AS3), as is represented in FIG. 10 by box 412.

It will be appreciated that the lens bodies of protective eyewear lens assemblies AS1, AS2 and/or AS3 can be formed from any suitable material or combination of materials. As one example, optically-transparent portions 106 of lens bodies 100 can be formed from an optically-clear (tinted or untinted, and coated or uncoated) polymeric material, such as a polycarbonate, for example. In accordance with the subject matter of the present disclosure, metal-detectable components, such as one or more of metal-detectable components 200, 200' and/or 200" can, in some cases, be at least partially formed from a polymeric material that has metal-detectable (e.g., conductively-detectable and/or magnetically-detectable) particles distributed substantially-evenly throughout the material. Additionally, or in the alternative, metal-detectable components, such as one or more of metal-detectable components 200, 200' and/or 200" can, in some cases, be at least partially formed from metallic material, such as steel, copper or brass that is metal-detectable (e.g., conductively-detectable and/or magnetically-detectable) and which can be coated or uncoated. It will be appreciated that such metal-detectable materials can be of any suitable size, shape, configuration and/or arrangement, such as thin sheets or foils, wire loops, wire segments and/or other bodies in regular (e.g., round, polygonal) and/or irregular shapes and/or cross-sections. Additionally, it will be appreciated that such metal-detectable materials can be formed in any suitable manner and/or by any combination of one or more processes, such as drawing, forging, stamping, molding, casting, cutting and/or milling, for example. In a preferred arrangement, optically-transparent portions 106 together with any additional portions (e.g., bridge portions 108) and/or components (e.g., temples 122) form the structural features of the protective eyewear with the one or more of metal-detectable components 200, 200' and/or 200", preferably, forming non-structural features of the protective eyewear assemblies.

Additionally, it will be appreciated that metal-detectable components can be formed from any suitable material or combination of materials, such as one or more materials that can be detected or are detectable using conventional systems, equipment and/or techniques for identifying foreign material in manufacturing and/or food production processes (e.g., magnetically-detectable and/or otherwise metal-detectable). Additionally, conventional systems employ widely adopted test standards associated with the use and operation of conventional systems. As non-limiting examples, one or more of metal-detectable components 200, 200' and/or 200" could be at least partially formed from a metal material and/or a metal-infused polymeric material having a metal detectability equivalent to at least a 3 mm metal sphere. In some cases, the one or more metal-detectable components can have a collective, total metal detectability equivalent to at least a 3 mm metal sphere. In other cases, each of the one or more metal-detectable components can have a metal detectability equivalent to at least a 3 mm metal sphere. In preferred arrangement, the one or more metal-detectable components can have a collective, total metal detectability equivalent to at least a 2 mm metal sphere. In some such cases, each of the one or more metal-detectable components can have a metal detectability equivalent to at least a 2 mm metal sphere. In a more preferred arrangement, the one or more metal-detectable components can have a collective, total metal detectability equivalent to at least a 1 mm metal sphere. In other cases, each of the one or more metal-detectable components can have a metal detectability equivalent to at least a 1 mm metal sphere.

As used herein with reference to certain features, elements, components and/or structures, numerical ordinals (e.g., first, second, third, fourth, etc.) may be used to denote different singles of a plurality or otherwise identify certain features, elements, components and/or structures, and do not imply any order or sequence unless specifically defined by the claim language.

Furthermore, terms such as "transverse" and the like, if used herein, are to be broadly interpreted to include a wide range of relative angular orientations that include, but are not limited to, an approximately perpendicular angular orientation. Also, terms such as "circumferential," "circumferentially," and the like, if used herein, are to be broadly interpreted and can include, but are not limited to circular shapes and/or configurations. In this regard, terms such as "circumferential," "circumferentially," and the like, can be synonymous with terms such as "peripheral," "peripherally," and the like.

Further still, the phrase "flowed-material joint" and the like, if used herein, are to be interpreted to include any joint or connection in which a liquid or otherwise flowable material (e.g., a melted metal or combination of melted metals) is deposited or otherwise presented between adjacent component parts and operative to form a fixed and substantially fluid-tight connection therebetween. Examples of processes that can be used to form such a flowed-material joint include, without limitation, welding processes, brazing processes and soldering processes. In such cases, one or more metal materials and/or alloys can be used to form such a flowed-material joint, in addition to any material from the component parts themselves. Another example of a process that can be used to form a flowed-material joint includes applying, depositing or otherwise presenting an adhesive between adjacent component parts that is operative to form a fixed and substantially fluid-tight connection therebetween. In such case, it will be appreciated that any suitable adhesive material or combination of materials can be used, such as one-part and/or two-part epoxies, for example.

It will be recognized that numerous different features and/or components are presented in the embodiments shown and described herein, and that no one embodiment may be specifically shown and described as including all such features and components. As such, it is to be understood that the subject matter of the present disclosure is intended to encompass any and all combinations of the different features and components that are shown and described herein, and, without limitation, that any suitable arrangement of features and components, in any combination, can be used. Thus, it is to be distinctly understood claims directed to any such combination of features and/or components, whether or not specifically embodied herein, are intended to find support in the present disclosure. To aid the Patent Office and any readers of this application and any resulting patent in interpreting the claims appended hereto, Applicant does not intend any of the appended claims or any claim elements to invoke 35 U.S.C. 112(f) unless the words "means for" or "step for" are explicitly used in the particular claim.

Thus, while the subject matter of the present disclosure has been described with reference to the foregoing embodiments and considerable emphasis has been placed herein on the structures and structural interrelationships between the component parts of the embodiments disclosed, it will be appreciated that other embodiments can be made and that many changes can be made in the embodiments illustrated and described without departing from the principles hereof. Obviously, modifications and alterations will occur to others upon reading and understanding the preceding detailed description. Accordingly, it is to be distinctly understood that the foregoing descriptive matter is to be interpreted merely as illustrative of the subject matter of the present disclosure and not as a limitation. As such, it is intended that the subject matter of the present disclosure be construed as including all such modifications and alterations.

The invention claimed is:

1. A protective eyewear lens assembly comprising:
   a metal-detectable component having a cross-sectional shape with at least a first component surface portion, a second component surface portion oriented offset from and aligned with said first component surface portion, and a third component surface portion disposed between and aligned with said first and second component surface portions, said metal-detectable component extending through an elongated length with a first elongated section and a second elongated section extending from along said first elongated section in a transverse orientation relative to said first elongated section, said metal-detectable component having said cross-sectional shape extending commonly along both said first and second elongated sections; and,
   a lens body formed in-situ around said metal-detectable component from a polymeric material, said lens body including a first lens surface portion and a second lens surface portion spaced from said first lens surface portion such that a lens thickness is defined therebetween with at least said third component surface portion of said cross-sectional shape of said metal-detectable component positioned within said polymeric material inward of said first and second lens surface portions such that said metal-detectable component is permanently embedded within said lens body and thereby resisting displacement of said metal-detectable component relative to said lens body in at least a lens thickness direction.

2. A protective eyewear lens assembly according to claim 1, wherein said metal-detectable component is one of a plurality of metal-detectable components permanently embedded within said lens body, said plurality of metal-detectable components having a total metal detectability equivalent to at least a 1 mm ferrous sphere.

3. A protective eyewear lens assembly according to claim 2, wherein each of said plurality of metal-detectable components has a metal detectability equivalent to at least a 1 mm ferrous sphere.

4. A protective eyewear lens assembly according to claim 1, wherein said lens body is at least partially formed from an optically-transparent polymeric material, and said lens body includes first and second optically-transparent portions at least partially formed from said optically-transparent polymeric material with a bridge portion disposed between said first and second optically-transparent portions.

5. A protective eyewear lens assembly according to claim 1, wherein said lens body extends in a widthwise direction between opposing first and second ends, and said lens body includes first and second optically-transparent portions, a bridge portion disposed between said first and second optically-transparent portions, a first hinge connection portion along said first end and a second hinge connection portion along said second end with said first and second hinge connection portions each unitarily formed from said polymeric material together with said bridge portion and/or at least one of said optically-transparent portions and with each of said first and second hinge connection portions operable to directly receive an associated ear-engaging temple.

6. A protective eyewear lens assembly according to claim 1, wherein said lens body includes an outer peripheral edge, and said metal-detectable component is disposed adjacent said outer peripheral edge.

7. A protective eyewear lens assembly according to claim 6, wherein said metal-detectable component is one of a plurality of metal-detectable components permanently embedded within said lens body with each of said plurality of metal-detectable components disposed adjacent said outer peripheral edge.

8. A protective eyewear lens assembly according to claim 7, wherein said lens body includes a top segment of said outer peripheral edge with at least one of said plurality of metal-detectable components permanently embedded within said lens body along said top segment of said outer peripheral edge.

9. A protective eyewear lens assembly according to claim 7, wherein said lens body includes a bottom segment of said outer peripheral edge with at least one of said plurality of metal-detectable components permanently embedded within said lens body along said bottom segment of said outer peripheral edge.

10. A protective eyewear lens assembly according to claim 1, wherein said lens body includes an outer peripheral edge and extends in a widthwise direction between opposing first and second ends as well as a heightwise direction oriented transverse to said lens thickness and said widthwise direction, said outer peripheral edge including a top edge segment and a bottom edge segment spaced in said heightwise direction from said top edge segment, said outer peripheral edge also including a first outer edge segment disposed along said first end and a second outer edge segment disposed along said second end with said metal-detectable component permanently embedded within said lens body such that said first elongated section extends in said widthwise direction along one of said top edge segment and said bottom edge segment and such that said second elongated section of said metal-detectable component extends along one of said first outer edge segment and said second outer edge segment.

11. A protective eyewear lens assembly according to claim 1, wherein said first component surface portion is exposed along one of said first lens surface portion and said second lens surface portion of said lens body, and said second component surface portion is exposed along the other of said first lens surface portion and said second lens surface portion of said lens body.

12. A protective eyewear lens assembly according to claim 1, wherein said metal-detectable component includes a fourth component surface portion disposed between and in offset alignment with said first and second component surface portions and embedded within said lens body.

13. A protective eyewear lens assembly according to claim 1, wherein said cross-sectional shape of said metal-detectable component is taken transverse to said first and second surface portions with said cross-sectional shape having one of an approximately T-shaped configuration and an approximately H-shaped configuration.

14. A protective eyewear lens assembly according to claim 1, wherein said lens body includes first and second optically-transparent portions, a bridge portion disposed between said first and second optically-transparent portions, an outer peripheral edge and a body periphery wall portion all unitarily formed from said polymeric material of said lens body, said body periphery wall portion extending peripherally around at least a portion of at least one of said first and second optically-transparent portions, said body periphery wall portion disposed between said outer peripheral edge and at least said portion of said at least one of said first and second optically-transparent portions with said body periphery wall portion having one of a frosted surface treatment, a colored external appearance, an opaque external appearance and less optical transparency than said first and second optically-transparent portions.

15. A protective eyewear assembly comprising:
a lens assembly including:
a metal-detectable component having a cross-sectional shape with at least a first component surface portion, a second component surface portion offset from and approximately aligned with said first component surface portion, and a third component surface portion disposed between and in offset alignment with said first and second component surface portions, said metal-detectable component extending through an elongated length with a first elongated section and a second elongated section extending from along said first elongated section in a transverse orientation relative to said first elongated section, said metal-detectable component having said cross-sectional shape extending commonly along both said first and second elongated sections; and,
a lens body formed in-situ around said metal-detectable component from a polymeric material such that said metal-detectable component is permanently embedded within said lens body, said lens body including a first lens surface portion facing an associated wearer during use and a second lens surface portion facing away from the associated wearer during use such that a lens thickness is defined therebetween, said third component surface portion of said cross-sectional shape of said metal-detectable component disposed within said polymeric material inward of said first and second lens surface portions and thereby resisting displacement of said metal-detectable component relative to said lens body in a thickness direction, said lens body extending in a widthwise direction between opposing first and second ends with a first hinge connection portion along said first end and a second hinge connection portion along said second end, said first and second hinge connection portions each unitarily formed from said polymeric material together with said lens body;
a first temple pivotally attached directly to said first hinge connection portion of said lens body; and,
a second temple pivotally attached directly to said second hinge connection portion of said lens body.

16. A protective eyewear assembly according to claim 15, wherein said metal-detectable component is one of a plurality of metal-detectable components permanently embedded within said lens body of said lens assembly and said plurality of metal-detectable components have a total metal detectability equivalent to at least a 1 mm ferrous sphere.

17. A protective eyewear assembly according to claim 15, wherein said lens body includes first and second optically-transparent portions, a bridge portion disposed between said first and second optically-transparent portions, an outer peripheral edge, and a body periphery portion unitarily formed from said polymeric material of said lens body and extending peripherally around at least a portion of at least one of said first and second optically-transparent portions, said body periphery portion disposed between said outer peripheral edge and at least said portion of said at least one of said first and second optically-transparent portions with said body periphery portion including one of a frosted surface treatment, a colored external appearance, an opaque external appearance and less optical transparency than said first and second optically-transparent portions.

18. A protective eyewear assembly according to claim 15, wherein said first component surface portion of said metal-detectable component is exposed along one of said first lens surface portion and said second lens surface portion of said lens body, said second component surface portion disposed toward the other of said first lens surface portion and said second lens surface portion of said lens body.

19. A protective eyewear assembly according to claim 18, wherein said metal-detectable component has a cross-sectional shape taken transverse to said first and second component surface portions with said cross-sectional shape having one of an approximately T-shaped configuration and an approximately H-shaped configuration.

20. A protective eyewear lens assembly comprising:
first and second metal-detectable components each formed from an elongated length of metal-detectable material and each including a first elongated portion and a second elongated portion extending transverse from along said first elongated portion, each of said first and second metal-detectable components including a common cross-sectional shape that extends along said first and second elongated portions of said elongated lengths thereof with said common cross-sectional shape including at least a first surface portion, a second surface portion offset from and approximately aligned with said first surface portion, and a third surface portion disposed between and approximately aligned with said first and second surface portions; and, a lens body extending in a widthwise direction between opposing first and second ends, said lens body including a first lens surface portion and a second lens surface portion spaced from said first lens surface portion such that a lens thickness is defined therebetween, said lens body including first and second optically-transparent portions, a bridge portion disposed between said first and second optically-transparent portions, a first hinge connection portion along said first end and a second hinge connection portion along said second end with each of said first and second optically-transparent portions, said bridge portion and said first and second hinge connection portions unitarily formed together from a single mass of polymeric material, said lens body formed in-situ from said single mass of polymeric material around said first and second metal-detectable components such that said first metal-detectable component is disposed within said first optically-transparent portion and said second metal-detectable component is disposed within said second optically-transparent portion with at least said third surface portion of said cross-sectional shape of each of said first and second metal-detectable components positioned within said single mass of polymeric material inward of said first and second lens surface portions permanently embedding said plurality of metal-detectable components within said lens body.

* * * * *